United States Patent [19]

Eyssautier

[11] Patent Number: 4,940,663

[45] Date of Patent: Jul. 10, 1990

[54] FERMENTATION PROCESS FOR THE PRODUCTION OF XANTHANE

[75] Inventor: Bruno Eyssautier, Carentan, France

[73] Assignee: SANOFI, Societe Anonyme, Paris, France

[21] Appl. No.: 209,932

[22] Filed: Jun. 22, 1988

[30] Foreign Application Priority Data

Jun. 22, 1987 [FR] France .............................. 87 08727

[51] Int. Cl.$^5$ ........................ C12P 19/06; C12N 1/20
[52] U.S. Cl. ................................ 435/104; 135/910; 514/54; 536/114
[58] Field of Search ................ 435/104, 910; 514/54; 536/114

[56] References Cited

U.S. PATENT DOCUMENTS

| | | | |
|---|---|---|---|
| 3,000,790 | 9/1961 | Jeanes et al. | |
| 3,271,267 | 9/1966 | Weber et al. | |
| 3,335,447 | 8/1967 | Olson et al. | |
| 3,427,226 | 2/1969 | McNeely | |
| 3,671,398 | 6/1972 | Colin et al. | 435/104 |
| 4,104,123 | 8/1978 | Duc et al. | 435/104 |
| 4,299,825 | 11/1981 | Lee | 435/104 |
| 4,394,447 | 7/1983 | Cadmus et al. | 435/104 |

OTHER PUBLICATIONS

*The Merck Index*, 10th ed., Merck & Co., Inc., 1983, No. 4242, "Gelatin".

*Primary Examiner*—Jacqueline Stone
*Assistant Examiner*—Jean Witz
*Attorney, Agent, or Firm*—Foley & Lardner, Schwartz, Jeffery, Schwaab, Mack, Blumenthal & Evans

[57] ABSTRACT

The invention relates to a process for the fermentation of carbohydrates by bacteria of the genus Xanthomonas for the production of a polysaccharide of the xanthane type, in which the source of nitrogen consists of a gelatin with a molecular weight of less than 5000.

Application: preparation of xanthane.

6 Claims, No Drawings

FERMENTATION PROCESS FOR THE PRODUCTION OF XANTHANE

The present invention relates to a process for the fermentation of carbohydrates for the preparation of a polysaccharide of the xanthane type by means of microorganisms of the Xanthomonas type, and to the polysaccharide obtained by this process.

It is known that the aerobic fermentation of bacteria of the Xanthomonas type in aqueous media with a pH of between 5.5 and 9, containing at least one source of carbon, a source of nitrogen, phosphate ions and trace elements, makes it possible to obtain a polysaccharide composition of the xanthane type. The source of carbon generally consists of carbohydrates, while the following have been described as sources of nitrogen: dry distillery draff in U.S. Pat. No. 3,000,790, peptones in TAPPI 5, p. 442–445, by M. O. BAGBY, I. A. WOLFF and M. C. CADMUS, yeast extracts in Biotechnol. Bioeng. (1971) 13, p. 381, by R. A. MORAINE and P. ROGOVIN, maceration liquors in U.S. Pat. No. 3,335,447 or soya bean flours in U.S. Pat. No. 3,271,267; cereal flours, such as sorghum flours, provide both the source of carbon and the source of nitrogen, as described in U.S. Pat. No. 3,271,267.

The products commonly used as sources of nitrogen introduce insoluble impurities into the medium, which appear in the polysaccharide isolated at the end of fermentation, this implying, for certain applications of the polysaccharide, treating the resulting product by various processes, for example filtration or flocculation, in order to remove these insoluble impurities which lead to the formation of cloudiness in aqueous polysaccharide solutions.

Furthermore, on the strength of its thickening property which is virtually independent of temperature and pH, xanthane is used in the assisted recovery of petroleum, as an edible additive in pharmaceutical or cosmetic formulations, or in the preparation of textiles or explosives, and it is of particular importance to have a grade of xanthane having naturally a high thickening property i.e. having aqueous solutions of high viscosity.

The present invention relates to a fermentation process which, through the use of a suitably chosen source of nitrogen, makes it possible to obtain a polysaccharide of xanthane type with a high thickening property, which contains few insoluble materials and whose aqueous solutions are clear and only very slightly colored, which is advantageous for numerous applications.

According to the invention, gelatin, and more particularly a gelatin of low molecular weight, is used as the source of nitrogen soluble in aqueous media. Two types of gelatin are known to exist: type A gelatin, which is obtained by the acid hydrolysis, for example with sulfuric acid, of the collagen present in the skin or bones of pigs and cattle, and type B gelatin, which is obtained by the basic hydrolysis of collagen, especially with Ca(OH)$_2$. The common gelatins, with a molecular weight greater than or equal to 20000 are known sources of nitrogen but they do not make it possible to achieve the advantageous results of the invention. It is desirable to use gelatins with an average molecular weight of less than 5000, having practically no gelling strength; the hydrolyzed gelatins with a molecular weight between 1500 and 2500 are particularly preferred.

It is possible to introduce into the fermentation medium a gelatin which has been hydrolyzed beforehand either by heating in an aqueous acid medium at a pH < 4 and at a temperature above 100° C., or through the enzymatic action of a protease in the manner described in French patent 1.501.821.

However, the gelatin can also be at least partially hydrolyzed during the sterilization of the culture medium, before the microorganisms are introduced, if the pH, temperature and heating time are suitably chosen; in this case, it is preferred initially to introduce gelatins whose molecular weight, before hydrolyzing sterilization, is no greater than 10.000.

When sterilization is carried out at an essentially neutral pH or at a slightly acid pH, for very short times of less than 5 minutes, the gelatin used must have a molecular weight of less than 5000, preferably less than 3000.

The amount of gelatin introduced into the fermentation medium is chosen so as to give a total nitrogen content of 0.1 g/l to 1 g/l.

The medium can also contain, in conventional manner, from 5 g/l to 50 g/l of carbohydrates such as glucose, native or hydrolyzed starches, sucrose, levulose, fructose, maltose, sugar beet molasses or sugar cane molasses, as well as 0.10 to 20 g/l, preferably 0.5 to 5 g/l, of phosphates such as K$_2$HPO$_4$, and one or more trace elements, including magnesium at a concentration of 0.025 to 1 g/l of magnesium in the form of a soluble magnesium salt such as magnesium sulfate, acetate, chloride or nitrate.

The bacteria which make it possible to obtain a xanthane by fermentation in these media are generally of the genus Xanthomonas and can belong to different species such as *Xanthomonas begoniae, Xanthomonas incanae, Xanthomonas vesicatoria, Xanthomonas campestris* and *Xanthomonas phaseoli*, and other species well known to those skilled in the art; strains of *Xanthomonas campestris* are generally used.

Fermentation is carried out at a pH which can be between 5.5 and 9 and is preferably between 6.5 and 8. at a temperature between 25° C. and 35° C. and preferably between 27° C. and 32° C. The medium is agitated and aerated in conventional manner; under these conditions, fermentation takes 1 to 6 days.

In a conventional manner, the process used to obtain the polysaccharide according to the invention comprises several steps:

1. Preparation of an inoculum from a strain of Xanthomonas which was previously quick-frozen or lyophilized;

2. If appropriate, growing of the microorganisms in a prefermentation medium;

3. Production of the polysaccharide in the fermentation medium, which has been inoculated with the media obtained in step 1 or 2 and;

4. Isolation of the polysaccharide.

The polysaccharide is generally isolated by precipitation through the introduction into the fermentation medium of a solvent in which the polysaccharide is insoluble. Among the solvents generally used, there may be mentioned lower alcohols such as methanol, ethanol, isopropanol and butanol, or acetone; isopropanol is preferred. Before the precipitation step, it is possible to heat the reaction medium at a temperature between 80° C. and 130° C. for a few minutes in order to destroy the bacteria.

A further possibility is to treat the medium before or after sterilization, with an aliphatic diaidehyde such as glyoxal, which is a known way of improving the dispersibility of polysaccharides in water; the xanthane is then precipitated in the medium, isolated by filtration, washed with the precipitating solvent and then dried and ground if necessary. In this case, 0.1 to 1% by weight of glyoxal is used, relative to the weight of dry xanthane; in general, about 2% is used. The xanthane can also be treated with a dialdehyde after isolation, if this operation has not already been carried out in the fermentation medium. An advantageous process consists in wetting the xanthane powder with a solution of glyoxal in aqueous isopropanol, prepared by mixing 5 to 10 ml of a 30% aqueous solution of glyoxal with 150 ml of isopropanol; after a contact time of 20 to 40 minutes, the solvents are removed by heating and the dry polysaccharide can then be stored for subsequent use in its conventional applications.

To improve the fermentation conditions and, in particular, to reduce the viscosity of the medium, fermentation on gelatin can also be carried out in the presence of an oil and a surfactant, by a process described in European patent application A-58364, which uses a water-in-oil emulsion as fermentation medium or a process described in European patent application A-187092, which uses an oil-in-water emulsion as fermentation medium.

The invention further relates to the polysaccharide composition of the xanthane type which is obtained by the fermentation process according to the invention.

This polysaccharide composition, like all products of this type, consists of saccharide units of the mannose, glucose and salified glucuronic acid type; some of the hydroxyl groups are esterified with acetic acid, and pyruvic acid is bonded via an acetal group to some of the mannose units. The polysaccharide composition according to the invention has a molecular weight of more than 2,000,000.

Its aqueous solutions have a particularly high viscosity which is greater than that of solutions of the xanthane produced by fermentation in a medium containing soya bean flour or corn maceration liquors as the source of nitrogen.

Thus an aqueous solution containing 1% by weight of KCl and 0.2% by weight of the polysaccharide of the invention has a viscosity of at least 200 mPa.s, measured on a Brookfield viscometer at 24° C., whereas, under the same conditions, that of an aqueous solution of the polysaccharide obtained by fermentation on soya bean flour is about 160 mPa.s.

The aqueous solutions of the invention polysaccharide have a low optical density. For example, the solutions containing 0.2% by weight of polysaccharide have an optical density, measured at 620 nm, less than or equal to 0.2.

An Example of the way in which the invention is carried out is now described below.

EXAMPLE (a) Preparation of the inoculum:

A revitalization culture medium MY consisting

| Glucose | 10.0 g |
| Pentone | 0.5 g |
| Yeast extract | 0.3 g |
| Malt extract | 3.0 g |
| Distilled water | 1000 g | sterilized beforehand by heating for 20 min at 120° C., is inoculated with 3 ml of defrozen bacteria of the *Xanthomonas campestris* strain deposited under no. NRRL.B 1459.

After inoculation, the medium is incubated at 30° C. for 12 to 18 hours, with agitation.

(b) Prefermentation

The microorganisms of the inoculum are then grown in a preculture fermentor containing 10 l of a medium consisting of:

| Glucose | 150.0 g |
| Gelatin | 20.0 g |
| $K_2HPO_4$ | 8.0 g |
| $MgSO_4$ | 1.8 g |
| Antifoam | 0 to 3.0 g |
| Water | qs for 10 l |

The glucose is sterilized beforehand by heating at pH 4, while the other constituents of the medium are sterilized as a mixture, for example by heating at 120° C. for 30 minutes at pH 4.5.

Prefermentation is continued for 20 hours before the inoculum is used to inoculate the fermentation medium.

(c) Fermentation and production of the polysaccharide:

The fermentation medium for a fermenter with a useful volume of 100 l consists of:

| Glucose | 3 kg |
| Gelatin | 200 g |
| $K_2HPO_4$ | 80 g |
| $MgSO_4$ | 18 g |
| Antifoam | 0 to 30 g |
| Water | qs for 100 l |

The glucose is sterilized on its own at pH 4, as previously, and the other constituents are sterilized at 120° C. for 30 minutes at different pH values, leading to gelatins with different molecular weights.

Before inoculation with the inoculum prepared in step b, the pH of the medium is adjusted to 7 and kept around this value throughout fermentation.

In a conventional manner, the medium is agitated and aerated throughout fermentation.

Table I indicates the results obtained using two type A gelatins with a molecular weight of 5000, no gelling strength and an isoelectric point of 6.3 or 6.6, hydrolyzed during sterilization at different pH values.

Gelatin 1 is marketed by Rousselot under the reference ASF and gelatin 2 under the reference HP50.

By way of comparison, a fermentation was also carried out using soya bean flour as the source of nitrogen.

The xanthane was precipitated at the end of the fermentation process by introducing 200 l of isopropanol into the medium; it was then filtered off and dried by heating in a stream of air.

TABLE I

| Source of nitrogen | Sterilization pH | Molecular weight | Fermentation time | Weight of xanthan g/kg of medium | Productivity g/l/h | Viscosity of the solution (a) mPa.s | Optical density (b) |
|---|---|---|---|---|---|---|---|
| Soya bean flour | 7 | | 47 h | 19.2 | 0.40 | 160 | 0.35 |
| Gelatin 1 | 7 | 5000 | 70 h | 5 | 0.071 | — | — |
| | 4 | 4000 | 63 h | 20 | 0.32 | 230 | 0.2 |
| | 2 | 2000 | 55 h | 22.6 | 0.41 | 205 | 0.194 |
| Gelatin 2 | 4 | 2500 | 54 h | 22.5 | 0.42 | 220 | 0.168 |
| | 2 | 2000 | 53 h | 22.7 | 0.43 | 225 | 0.174 |

(a) concentration: 0.2% by weight in aqueous solution containing 1% by weight of KCl; measured on a Brookfield viscometer at T = 24° C.
(b) in aqueous solution containing 0.2% by weight and measured at a wavelength of 620 nm.

What is claimed is:

1. A fermentation process for the production of xanthane which comprises the step of fermenting carbohydrates with bacteria of the genus Xanthomonas in a fermentation medium containing a nitrogen source, wherein said source of nitrogen consists of a partially hydrolyzed gelatin with a molecular weight of less than 5000, whereby the resulting xanthane has elevated viscosity per unit weight.

2. The fermentation process according to claim 1, wherein the partially hydrolyzed gelatin has a molecular weight between 1500 and 2500.

3. The fermentation process according to claim 1, wherein the bacteria belong to the species *Xanthomonas campestris*.

4. The fermentation process according to claim 1, wherein the medium comprises from 5 g/l to 50 g/l of carbohydrates, from 0.5 g/l to 5 g/l of $K_2HPO_4$, from 0.025 g/l to 1 g/l of magnesium and a sufficient amount of the partially hydrolyzed gelatin to provide from 0.1 g/l to 1 g/l of total nitrogen.

5. The fermentation process according to claim 1, wherein the gelatin is at least partially hydrolyzed during sterilization of the fermentation medium.

6. A fermentation process for the production of xanthane which comprises the steps of:
   (a) preparing an inoculum of bacteria of the genus Xanthomonas,
   (b) fermenting carbohydrates with bacteria of the genus Xanthomonas in a fermentation medium containing a nitrogen source, wherein said source of nitrogen consists of a partially hydrolyzed gelatin with a molecular weight of less than 5000; and
   (c) isolating the resultant xanthane having an elevated viscosity per unit weight.

* * * * *